United States Patent
Aimi

(10) Patent No.: US 8,574,316 B2
(45) Date of Patent: Nov. 5, 2013

(54) HAIR DYE

(75) Inventor: Makiko Aimi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/582,003

(22) PCT Filed: Feb. 28, 2011

(86) PCT No.: PCT/JP2011/054513
§ 371 (c)(1),
(2), (4) Date: Nov. 9, 2012

(87) PCT Pub. No.: WO2011/108491
PCT Pub. Date: Sep. 9, 2011

(65) Prior Publication Data
US 2013/0047349 A1      Feb. 28, 2013

(30) Foreign Application Priority Data
Mar. 1, 2010   (JP) ................................ 2010-044021

(51) Int. Cl.
*A61Q 5/10*   (2006.01)
(52) U.S. Cl.
USPC ................. 8/405; 8/521; 8/580; 8/595; 8/623
(58) Field of Classification Search
USPC ............................ 8/405, 521, 580, 595, 623
See application file for complete search history.

(56) References Cited

FOREIGN PATENT DOCUMENTS

| JP | 53-52633 | A |   | 5/1978 |
|---|---|---|---|---|
| JP | 4-164017 | A |   | 6/1992 |
| JP | 7-165542 | A |   | 6/1995 |
| JP | 2003-246716 | A |   | 9/2003 |
| JP | 2008-273869 | A |   | 11/2008 |
| JP | 2008273869 | A | * | 11/2008 |

OTHER PUBLICATIONS

English abstract of the Japanese Patent No. JP 2008273869 A dated Nov. 13, 2008.*
English translation of International Preliminary Report on Patentability dated Sep. 20, 2012 for International Application No. PCT/JP2011/054513.
International Preliminary Report on Patentability dated Sep. 13, 2012 for International Application No. PCT/JP2011/054513.
International Search Report dated May 24, 2011 for PCT/JP2011/054513.
Office Action dated Apr. 7, 2013 in Chinese Application No. 201180011771.5.
Tong Yi, The Progress on the Research of Permanent Hair Dyeing Agent, Chemical Industry Times, No. 5, pp. 4-8 (1999).
Chen, Xian-xuan et al, Action of Sorbitol on the Hydrolytic Polymerization of Ferric Ions and its Effect on the Masking Action of Citric Acid, Acta Pharmaceutica Sinica, vol. 18, No. 4, pp. 272-277 (1983).

* cited by examiner

*Primary Examiner* — Eisa Elhilo
(74) *Attorney, Agent, or Firm* — Sughrue Mion, PLLC

(57) ABSTRACT

Provided is a hair dye, which comprises a combination of (1) a first agent containing a substance reacting with iron to develop color, and (2) a second agent containing (a) an iron salt and (b) at least one component selected from among xylitol, sorbitol, pentylene glycol, dipropylene glycol, triethylene glycol, erythritol and diglycerin.

20 Claims, 1 Drawing Sheet

Position of Fe in dyed hair with high level of color loss (SEM image of hair section)

Position of Fe in dyed hair with low level of color loss (SEM image of hair section)

Position of Fe in dyed hair with high level of color loss (SEM image of hair section)
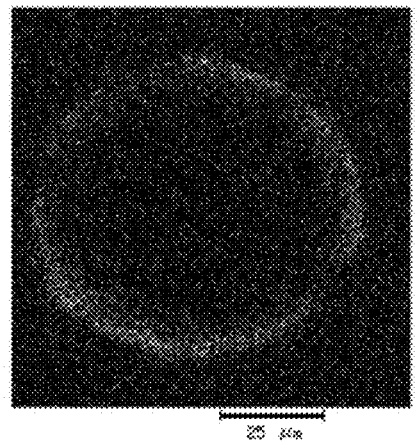
Position of Fe in dyed hair with low level of color loss (SEM image of hair section)
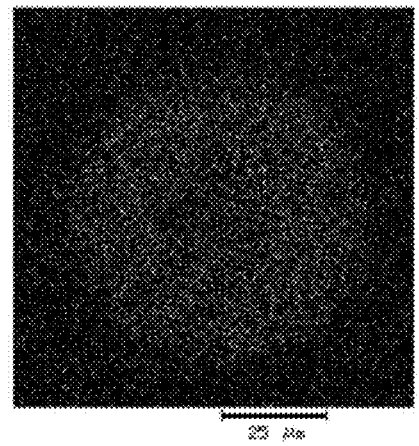

HAIR DYE

CROSS REFERENCE TO RELATED APPLICATIONS

This application is a National Stage of International Application No. PCT/JP2011/054513 filed on Feb. 28, 2011 which claims priority from Japanese Patent Application No. 2010-044021, filed on Mar. 1, 2010, the contents of all of which are incorporated herein by reference in their entirety.

TECHNICAL FIELD

The present invention relates to a non-oxidative hair dye, which has high preservation stability of an iron salt, and in which the loss of color due to shampooing is small because the inside of the hair can also be dyed as a result of a suitable reaction control.

BACKGROUND ART

Hair dye is generally classified into four types, namely, oxidative hair dye, ionic hair dye, temporary hair dye, and others. Among these hair dyes, an oxidative hair dye, which has been most widely used at present, is also referred to as a permanent hair dye, and it is mainly constituted with paraphenylenediamine or para-aminophenol that becomes an active reaction intermediate as a result of oxidation by hydrogen peroxide. The active intermediate then reacts with a dye coupler molecule in hair, and it changes to a shampoo-resistant hair dye. However, such an oxidative hair dye damages hair, may cause contact dermatitis or latent influence on total body for a long period of time, and may be suspected as mutagenicity or carcinogen. An ionic hair dye is also referred to as a semi-permanent hair dye, and it does not damage hair. However, such an ionic hair dye is problematic in term of skin coloration upon dyeing, and in that the dye is washed off by performing shampooing operations four to ten times. A temporary hair dye does not damage hair, and skin coloration is overcome by washing. However, such a temporary hair dye is washed off by performing a single shampooing operation.

As another hair dye, there has been proposed a non-oxidative hair dye containing polyvalent phenol and an iron salt (Patent Documents 1 to 3). However, previous non-oxidative hair dye products have not been satisfactory in terms of hair dyeing property and color tone, and have been problematic in terms of loss of color due to shampooing. In addition, the stability of an iron salt is low in an aqueous solution, and thus the iron salt is easily precipitated in a solution. As a result, it is difficult to produce a liquid-type non-oxidative hair dye containing an iron salt.

Moreover, it has been known that an organic acid is mixed to control a chelating reaction. As a result of the mixing of an organic acid, coloration of the skin is reduced. However, it has been problematic in that significantly decreased reactivity may cause degradation of the hair dyeing property (Patent Documents 4 and 5).

PRIOR ART DOCUMENTS

Patent Documents

Patent Document 1: JP Patent Publication (Kokai) No. 4-164017 A (1992)
Patent Document 2: JP Patent Publication (Kokai) No. 2003-246716 A
Patent Document 3: JP Patent Publication (Kokai) No. 2008-273869 A
Patent Document 4: JP Patent Publication (Kokai) No. 53-52633 A (1978)
Patent Document 5: JP Patent Publication (Kokai) No. 7-165542 A (1995)

SUMMARY OF INVENTION

Object to be Solved by the Invention

A conventional hair dye, which contains a plant extract or an organic compound that reacts with an ion salt to develop color, has been problematic in terms of loss of color due to shampooing, and in that its hair dyeing property and color tone have not been satisfactory. In addition, the conventional hair dye has also been problematic in that a dosage form cannot be freely selected because the solubility of an iron salt in water is low. It is an object of the present invention to provide a safe hair dye, which has high resistance to shampooing, a good dyeing property and good color tone, and which further has high preservation stability of an iron salt.

Means for Solving the Object

As a result of intensive studies directed towards achieving the aforementioned object, the present inventors have found that a hair dye, which has high preservation stability of an iron salt, and in which the loss of color due to shampooing is small because the inside of the hair can be dyed as a result of a suitable reaction control, can be provided by adding one or more components selected from among xylitol, sorbitol, pentylene glycol, dipropylene glycol, triethylene glycol, erythritol and diglycerin, to an iron salt, thereby completing the present invention.

The present invention provides a hair dye, which comprises a combination of (1) a first agent containing a substance reacting with iron to develop color, and (2) a second agent containing (a) an iron salt and (b) at least one component selected from among xylitol, sorbitol, pentylene glycol, dipropylene glycol, triethylene glycol, erythritol and diglycerin.

Preferably, the at least one component selected from among xylitol, sorbitol, pentylene glycol, dipropylene glycol, triethylene glycol, erythritol and diglycerin is added in an equimolar amount or more based on the amount of iron salt, and at a weight percentage of 20% or less based on the total weight of the second agent.

Preferably, the component described in (2) (b) is at least one component selected from among xylitol, sorbitol, pentylene glycol and dipropylene glycol.

Preferably, the component described in (2) (b) is at least one component selected from xylitol and sorbitol.

Preferably, the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, catechin, epicatechin, lithospenni radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, luteolinidin, and oxybenzone.

Preferably, the iron salt is ferrous sulfate, ferrous chloride, ferrous acetate, ferric sulfate, ferric chloride, or ferric acetate.

Preferably, the substance reacting with iron to develop color is used at a weight percentage of 0.5% to 10% based on the total weight of the first agent, and the iron salt is used at a weight percentage of 0.5% to 10% based on the total weight of the second agent.

The present invention further provides a method for dyeing hair, which comprises adding the aforementioned hair dye of the present invention to hair.

Effect of the Invention

Since permeation of pigments into the hair is promoted in the hair dye of the present invention, the present hair dye has high shampoo resistance, a good hair dyeing property and good color tone, and is also excellent in terms of the preservation stability of an iron salt.

BRIEF DESCRIPTION OF DRAWINGS

FIG. 1 shows the position of Fe in hair with a high level of color loss (a SEM image of a hair section) and the position of Fe in hair with a low level of color loss (a SEM image of a hair section).

EMBODIMENTS FOR CARRYING OUT THE INVENTION

Hereinafter, the embodiments for carrying out the present invention will be described in detail.

The hair dye of the present invention is a two-agent hair dye comprising a combination of (1) a first agent containing a substance reacting with iron to develop color, and (2) a second agent containing (a) an iron salt and (b) at least one component selected from among xylitol, sorbitol, pentylene glycol, dipropylene glycol, triethylene glycol, erythritol and diglycerin. The reaction control of iron with the use of an organic acid has been known. However, such reaction control reduces a hair dyeing property itself, and as a result, color development becomes deteriorated. In the present invention, reactivity can be suitably controlled by utilizing an extremely weak interaction between an iron salt and a polyhydric alcohol selected from among xylitol, sorbitol, pentylene glycol, dipropylene glycol, triethylene glycol, erythritol and diglycerin, and the preservation stability of an iron salt can also be improved. Moreover, the inside of the hair can also be dyed as a result of the reaction control, and thus, shampoo resistance can be improved.

As a substance reacting with iron to develop color used in the present invention, an organic compound or a plant extract that reacts with iron to develop color can be used. Specific examples of such a substance reacting with iron to develop color include, but are not limited to, tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, and luteolinidin. Among the above substances, more preferred examples include tannic acid, gallic acid and a derivative thereof, salicylic acid and a derivative thereof, ferulic acid, turmeric extract, Scutellaria root extract, quercetin, oxybenzone-1 (2,4-dihydroxybenzophenone), oxybenzone-3 (2-hydroxy-4-methoxybenzophenone), oxybenzone-4 (2-hydroxy-4-methoxybenzophenone sulfonate), oxybenzone-6 (2,2'-dihydroxy-4,4'-dimethoxybenzophenone), tetrahydroxybenzophenone, oxybenzone-9 (2,2'-dihydroxy-4,4'-dimethoxybenzophenone disulfonate), 4-ethoxy-2-hydroxybenzophenone, 4-(2-ethylhexyloxy)-2-hydroxybenzophenone, 5-amino-2-hydroxybenzophenone, 4-amino-2-hydroxybenzophenone, 4'-amino-2-hydroxybenzophenone, 2-hydroxy-5-chlorobenzophenone, 2-hydroxy-3,5-dichlorobenzophenone, 3',5-dichloro-2-hydroxy-benzophenone, 2-hydroxy-4'-methylbenzophenone, 2-hydroxy-4'-methoxybenzophenone, 2-hydroxy-5-methylbenzophenone, 2-hydroxy-4'-methylbenzophenone, and 2-hydroxy-3-tert-butyl-benzophenone. Further preferred examples include tannic acid, gallic acid or a derivative thereof, salicylic acid or a derivative thereof, Scutellaria root extract, hematein, turmeric extract, quercetin, tea extract, laccaic acid, kaoliang, oxybenzone-3, and oxybenzone-4. An example of the gallic acid derivative is an alkyl ester of gallic acid. An example of the gallic acid alkyl ester is a linear or branched alkyl ester containing 1 to 10, and preferably 2 to 5 carbon atoms. Specific examples of such a gallic acid alkyl ester include ethyl gallate, propyl gallate, and isoamyl gallate. Such gallic acid or a derivative thereof may be chemically synthesized according to a known method, or it may also be isolated from a plant. Moreover, it may also be prepared by further performing chemical synthesis on gallic acid or a derivative thereof isolated from a plant. Furthermore, an extract containing the gallic acid or a derivative thereof isolated from a plant may be directly used. For example, gallic acid derived from *Aralia elata* as a leguminous plant, gallic acid derived from gallnut produced from *Rhus javanica* as an anacardiaceous plant, or an extract containing the same may be used. Still further, a derivative obtained by chemically esterifying such gallic acid may also be used. Examples of the salicylic acid derivative include esters and salts of salicylic acid. Examples of the salicylic acid salt include alkali metal salts of salicylic acid. A specific example is sodium salicylate. Examples of the salicylic acid ester include methyl salicylate and ethyl salicylate.

The amount of the substance reacting with iron to develop color used is not particularly limited, as long as the effects of the present invention are obtained. The substance is used at a weight percentage of preferably 0.5% to 10%, and more preferably 1% to 6%, based on the total weight of the first agent.

The type of the iron salt used in the present invention is not particularly limited, as long as the effects of the present invention can be obtained. In general, ferrous sulfate, ferrous chloride, ferrous acetate, ferric sulfate, ferric chloride, ferric acetate, or the like can be used. Of these, ferrous sulfate or ferric chloride is preferable.

The amount of the iron salt used is not particularly limited, as long as the effects of the present invention can be obtained. The iron salt is used at a weight percentage of preferably 0.5% to 10%, and more preferably 1% to 6%, based on the total weight of the second agent.

The second agent used in the present invention contains at least one component selected from among xylitol, sorbitol, pentylene glycol, dipropylene glycol, triethylene glycol, erythritol and diglycerin. Among the aforementioned components, xylitol, sorbitol, pentylene glycol and dipropylene glycol are preferable, and xylitol and sorbitol are particularly preferable. The aforementioned components may also be used in combination of two or more components.

The at least one component selected from among xylitol, sorbitol, pentylene glycol, dipropylene glycol, triethylene glycol, erythritol and diglycerin is used in an equimolar amount or more based on the iron salt, and at a weight percentage of 20% or less based on the total weight of the second agent.

The first agent and/or second agent that constitute(s) the hair dye of the present invention may also comprise various types of additives, in addition to the aforementioned compounds. Examples of the additives include a base, a surfactant, oils and fats, a solvent, a thickener, organic acid, an antiseptic, an antioxidant, a pH adjuster, a wetting agent, perfume, a metallic taste masking agent, a coloring agent for products, and an ultraviolet absorber for products. As such additives, ingredients used for ordinary cosmetic products, such as a hair restorer/hair growth stimulant, an anti-dandruff agent, an antibacterial agent, a softener, a moisturizer, an active oxygen removing agent, an antioxidant, an antimicrobial agent, silicone, mineral, a protein hydrolysate, a peptide, and amino acids, may be mixed, as appropriate, within a range that does not impair the object of the present invention. The amounts of these additives used may be determined, as appropriate, within a range in which the effects of the present invention are exhibited.

Examples of the base include higher alcohols, hydrocarbon, fatty acid ester, vegetable oil, and fatty acid. Examples of the surfactant include polyoxyethylene alkyl ether, polyoxyethylene polyoxypropylene alkl ether, glycerin fatty acid ester, polyglycerin fatty acid ester, polyethylene glycol fatty acid ester, polyoxyethylene alkyl ether phosphate and a salt thereof, alkylglucoside, N-acylamino acid salt, alkyl ether carboxylate, alkyl sulfate, polyoxyethylene alkyl ether sulfate, sulfonate, alkyl ammonium salt, and alkyl amide propyl betaine. Examples of the antioxidant include ascorbic acid and a derivative thereof, and sodium sulfite. Examples of the pH adjuster include ammonia, ammonium bicarbonate, ammonium carbonate, potassium hydroxide, sodium hydroxide, monoethanolamine, and isopropanolamine. Examples of the wetting agent include 1,3-butylene glycol, propylene glycol, glycerin, sodium pyrroridonecarboxylate, amino acid, and vegetable oil. Examples of the thickener include xanthan gum, polyethylene glycol, and hydroxyethyl cellulose. Examples of the solvent include water, ethanol, isopropyl alcohol, 1,3-butylene glycol, 2-methyl-2,4-pentanediol, glycerin, and propylene glycol.

The hair dye of the present invention is a two-agent hair dye that is composed of a first agent and a second agent, and hair dyeing is carried out by mixing the first agent with the second agent. The first agent comprises a substance reacting with iron to develop color, whereas the second agent comprises an iron salt, and at least one component selected from among xylitol, sorbitol, pentylene glycol, dipropylene glycol, triethylene glycol, erythritol and diglycerin.

The ratio between the first agent and the second agent is the first agent:the second agent=about 1:0.5 to 1:2 at a weight ratio, and particularly preferably, the first agent:the second agent=about 1:1 at a weight ratio.

The pH of the first agent is preferably pH 6 to 10, and more preferably pH 7 to 9. The pH of the second agent is preferably pH 2 to 6, and more preferably pH 3 to 5.

Examples of the dosage form of the hair dye of the present invention include cream, liquid, gel, emulsion, spray, and aerosol. Of these, aerosol is preferable. Such aerosol can be produced by filling a pressure-resistant container with the hair dye (the first agent or the second agent), compressed gas, a surfactant, a thickener, liquefied gas, etc. under an anaerobic atmosphere. The compressed gas used herein is preferably nitrogen gas, carbonic acid gas, argon gas, or the like.

Hair dyeing can be carried out by applying the above-described hair dye of the present invention to hair. As a method for applying the hair dye of the present invention to hair, the first agent may be first applied to the hair and may be then left for a predetermined period of time. Then, the second agent may be applied to the hair and may be then left for a predetermined period of time. Thereafter, the agents may be washed off. Alternatively, the first agent and the second agent may be simultaneously applied to hair, and may be then left for a predetermined period of time, followed by washing them off.

With regard to the amount of the hair dye of the present invention applied, it is preferable to apply approximately 30 to 70 g of the first agent and approximately 30 to 70 g of the second agent to hair with a length of approximately 20 cm. It is more preferable to apply approximately 40 to 60 g of the first agent and approximately 40 to 60 g of the second agent to the aforementioned hair. As an example, 50 g of the first agent and 50 g of the second agent may be applied.

Hereinafter, the present invention will be more specifically described in the following examples. However, these examples are not intended to limit the scope of the present invention.

EXAMPLES

Hair Dyeing Effects:

Hair dye compositions having the compositions shown in Tables 1 to 3 were produced by an ordinary method. The numerical value of each compound shown in the tables indicates % by weight based on the total weights of the first agent and the second agent. These compositions were evaluated in terms of hair drying property by the following methods. The results are shown in Tables 1 to 3. The amounts of sodium hydroxide and hydrochloric acid are amounts necessary for adjusting the pH to the values shown in the tables.

Hair Dyeing Method:

2 g of the first agent was applied to 1 g of a goat hair bundle (part number: manufactured by Beaulax) with a length of approximately 10 cm, and it was then spread thereon uniformly. Then, it was left for a predetermined period of time. Thereafter, 2 g of the second agent was applied thereto and was then spread thereon uniformly, followed by leaving it for a predetermined period of time. Thereafter, the hair bundle was subjected to shampooing and rinsing treatments, and it was then dried with a dryer.

Method for Evaluating Hair Dyeing Property:

The color of each dyed hair bundle was measured with Chroma Meter CR200 manufactured by Minolta Corp. Hair dyeing property was evaluated based on the color difference ($\Delta E$ value) from the original white hair in accordance with the following standards.

◎: 30<$\Delta E$ value (Goat hair is found fully colored by visual observation.)

○: 20<$\Delta E$ value<30 (Goat hair is found colored by visual observation)

×: $\Delta E$ value<10 (Goat hair is found hardly colored by visual observation)

Method for Evaluating Shampoo Resistance

The dyed hair bundles were subjected to shampooing and rinsing treatments, and were then dried with a dryer. Thereafter, the color of each dyed hair bundle was measured with Chroma Meter CR200 manufactured by Minolta Corp.

Shampoo resistance was evaluated based on the color difference (ΔE value) from the original hair bundle in accordance with the following standards.

⊚: ΔE value<3 (Loss of color is hardly found by visual observation)
◯: 3<ΔE value<6 (A small level of loss of color is found by visual observation)
Δ: 6<ΔE value<10 (Loss of color is found by visual observation)
x: ΔE value>10
–: The hair bundle has no hair dyeing property Method for Evaluating Stability of Second Agent
The second agent, which had been left for a certain period of time, was evaluated in accordance with the following standards.
⊚: Highly stable
◯: Stable
x: Unstable

TABLE 1

| | | Examples | | | | | | | | | |
|---|---|---|---|---|---|---|---|---|---|---|---|
| | | 1 | 2 | 3 | 4 | 5 | 6 | 7 | 8 | 9 | 10 |
| First agent | Sodium salicylate | 1.0 | 1.0 | 1.0 | 1.0 | 1.0 | 1.0 | 1.0 | 1.0 | 1.0 | 1.0 |
| | Tannic acid | 0.2 | 0.2 | 0.2 | 0.2 | 0.2 | 0.2 | 1.0 | 0.3 | 0.3 | 0.3 |
| | Propyl gallate | | | | | | | 0.3 | | | |
| | Hematein | | | | | | | | | | |
| | Tea extract | | | | | | | | | | |
| | Oxybenzone-3 | 2.0 | 2.0 | 2.0 | 2.0 | 2.0 | 2.0 | 2.0 | | | |
| | Scutellaria root extract | 0.2 | 0.2 | 0.2 | 0.2 | 0.2 | 0.2 | 0.2 | | | |
| | Turmeric extract | | | | | | | | 1.0 | 1.0 | 1.0 |
| | Quercetin | | | | | | | | | | 0.3 |
| | Kaoliang | | | | | | | | | | |
| | Oxybenzone-4 | | | | | | | | | | |
| | Ethanol | 5 | 5 | 5 | 5 | 5 | 5 | 5 | 5 | 5 | 5 |
| | Benzyl alcohol | 10 | 10 | 10 | 10 | 10 | 10 | 10 | 10 | 10 | 10 |
| | Sodium hydroxide | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance |
| | pH | 8 | 8 | 8 | 8 | 8 | 8 | 8 | 8 | 8 | 8 |
| | Leaving time | 15 | 15 | 15 | 15 | 15 | 15 | 15 | 15 | 15 | 15 |
| Second agent | Ferrous sulfate | 2.0 | 2.0 | 2.0 | 2.0 | 2.0 | 2.0 | 2.0 | | 2.0 | 2.0 |
| | Ferric chloride | | | | | | | | 2.0 | | |
| | Pentylene glycol | 5.0 | | | | | | 2.0 | 2.0 | 5.0 | 10.0 |
| | Dipropylene glycol | | 5.0 | | | | | | | 5.0 | |
| | Xylitol | | | 5.0 | | | | 10.0 | 10.0 | 2.0 | 5.0 |
| | Triethylene glycol | | | | 5.0 | | | | | | |
| | Erythritol | | | | | 5.0 | | | | 3.0 | |
| | Diglycerin | | | | | | 5.0 | | | | |
| | Sodium hydroxide | q.s. | q.s. | q.s. | q.s. | q.s. | q.s. | q.s. | q.s. | q.s. | q.s. |
| | Hydrochloric acid | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance |
| | pH | 4 | 3.5 | 4 | 4 | 4 | 5 | 4 | 4 | 4 | 4 |
| | Leaving time | 15 | 15 | 15 | 15 | 15 | 15 | 15 | 15 | 15 | 15 |
| Hair dyeing Results | | ⊚ | ⊚ | ⊚ | ⊚ | ⊚ | ⊚ | ⊚ | ⊚ | ⊚ | ⊚ |
| Shampoo resistance | | ◯ | ◯ | ◯ | ◯ | ◯ | ◯ | ⊚ | ⊚ | ⊚ | ⊚ |
| Stability of second agent | | ◯ | ◯ | ⊚ | ◯ | ◯ | ◯ | ⊚ | ⊚ | ⊚ | ⊚ |

TABLE 2

| | | Examples | | | | | | | | | |
|---|---|---|---|---|---|---|---|---|---|---|---|
| | | 11 | 12 | 13 | 14 | 15 | 16 | 17 | 18 | 19 | 20 |
| First agent | Sodium salicylate | | | | 1.0 | 1.0 | 1.0 | 1.0 | 1.0 | | |
| | Tannic acid | 0.1 | 0.1 | 0.1 | 0.1 | 0.1 | 0.1 | | | 0.1 | 0.1 |
| | Propyl gallate | | | | | | | | | | |
| | Hematein | | | | | | | | 2.0 | | |

TABLE 2-continued

| | | Examples | | | | | | | | | |
|---|---|---|---|---|---|---|---|---|---|---|---|
| | | 11 | 12 | 13 | 14 | 15 | 16 | 17 | 18 | 19 | 20 |
| | Tea extract | | | | | | | | 2.0 | | |
| | Oxybenzone-3 | | 1.5 | 1.5 | 1.5 | | | | | | |
| | Scutellaria root extract | | | | | | | 0.3 | 0.3 | | |
| | Turmeric extract | 1.0 | 1.0 | 1.0 | 1.0 | 1.0 | 1.0 | | | 1.0 | 1.0 |
| | Quercetin | | | | | | | | 5.0 | | |
| | Kaoliang | | | | | | | | | 2.0 | |
| | Oxybenzone-4 | | | | | | | | | | 1.5 |
| | Ethanol | 5 | 5 | 5 | 5 | 5 | 5 | 5 | 5 | 5 | 5 |
| | Benzyl alcohol | 10 | 10 | 10 | 10 | 10 | 10 | 10 | 10 | 10 | 10 |
| | Sodium hydroxide | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance |
| | pH | 8 | 7 | 8 | 8 | 8 | 8 | 8 | 9 | 8 | 8 |
| | Leaving time | 15 | 15 | 15 | 15 | 15 | 15 | 15 | 15 | 15 | 15 |
| Second agent | Ferrous sulfate | 2.0 | 2.0 | 2.0 | 2.0 | 2.0 | 2.0 | 2.0 | 2.0 | 2.0 | 2.0 |
| | Ferric chloride | | | | | | | | | | |
| | Pentylene glycol | 3.0 | | | | | | 5.0 | | | 10.0 |
| | Dipropylene glycol | | 10.0 | | 5.0 | | | | | | |
| | Xylitol | | | 10.0 | 10.0 | 2.0 | 5.0 | | | 5.0 | 5.0 |
| | Triethylene glycol | | | | | | | | 5.0 | | |
| | Erythritol | | | | | | 3.0 | | | 5.0 | |
| | Diglycerin | | | | | | | 5.0 | | | |
| | Sodium hydroxide | q.s. | q.s. | q.s. | q.s. | q.s. | q.s. | q.s. | q.s. | q.s. | q.s. |
| | Hydrochloric acid | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance |
| | pH | 4 | 4 | 5 | 4 | 4 | 4 | 3.5 | 4 | 4 | 4 |
| | Leaving time | 15 | 15 | 15 | 15 | 15 | 15 | 15 | 15 | 15 | 15 |
| Hair dyeing Results | | ○ | ○ | ○ | ○ | ○ | ○ | ◎ | ◎ | ○ | ○ |
| Shampoo resistance | | ○ | ○ | ○ | ○ | ○ | ○ | ◎ | ◎ | ◎ | ◎ |
| Stability of second agent | | ○ | ○ | ◎ | ◎ | ◎ | ◎ | ○ | ○ | ◎ | ◎ |

TABLE 3

| | | Examples | | | | |
|---|---|---|---|---|---|---|
| | | 21 | 22 | 23 | 24 | 25 |
| First agent | Sodium salicylate | | | | 1.0 | 1.0 |
| | Tannic acid | 0.1 | 0.4 | 0.4 | 0.3 | 0.3 |
| | Oxybenzone-4 | 1.5 | 1.5 | 1.5 | 2.0 | 2.0 |
| | Ethanol | 5 | 5 | 5 | 5 | 5 |
| | Benzyl alcohol | 10 | 10 | 10 | 10 | 10 |
| | Sodium hydroxide | q.s. | q.s. | q.s. | q.s. | q.s. |
| | Purified water | Balance | Balance | Balance | Balance | Balance |
| | pH | 7 | 7 | 7 | 7 | 7 |
| | Leaving time | 15 | 15 | 15 | 15 | 15 |
| Second agent | Ferrous sulfate | 2.0 | 5.0 | 5.0 | 2.0 | 2.0 |
| | Xylitol | | | | | 2.0 |
| | Sorbitol | 3.0 | 5.0 | 10.0 | 5.0 | 5.0 |
| | Sodium hydroxide | q.s. | q.s. | q.s. | q.s. | q.s. |
| | Hydrochloric acid | q.s. | q.s. | q.s. | q.s. | q.s. |
| | Purified water | Balance | Balance | Balance | Balance | Balance |
| | pH | 4 | 4 | 5 | 4 | 4 |
| | Leaving time | 15 | 15 | 15 | 15 | 15 |
| Hair dyeing Results | | ○ | ◎ | ◎ | ◎ | ◎ |
| Shampoo resistance | | ○ | ○ | ○ | ○ | ○ |
| Stability of second agent | | ○ | ◎ | ◎ | ◎ | ◎ |

TABLE 4

| | | Comparative Examples | | | | | | | | | |
|---|---|---|---|---|---|---|---|---|---|---|---|
| | | 1 | 2 | 3 | 4 | 5 | 6 | 7 | 8 | 9 | 10 |
| First agent | Sodium salicylate | 1.0 | 1.0 | 1.0 | 1.0 | | 1.0 | 1.0 | 1.0 | | |

TABLE 4-continued

|  |  | Comparative Examples | | | | | | | | | |
|---|---|---|---|---|---|---|---|---|---|---|---|
|  |  | 1 | 2 | 3 | 4 | 5 | 6 | 7 | 8 | 9 | 10 |
|  | Tannic acid | 0.2 | 1.0 | 0.3 | 0.3 | 0.1 | 0.1 |  |  | 0.1 | 0.1 |
|  | Propyl gallate |  | 0.3 |  |  |  |  |  |  |  |  |
|  | Hematein |  |  |  |  |  |  | 2.0 |  |  |  |
|  | Tea extract |  |  |  |  |  |  |  | 2.0 |  |  |
|  | Oxybenzone-3 | 2.0 | 2.0 |  |  | 1.5 |  |  |  |  |  |
|  | Scutellaria root extract | 0.2 | 0.2 |  |  |  |  |  | 0.3 | 0.3 |  |
|  | Turmeric extract |  |  | 1.0 | 1.0 | 1.0 | 1.0 |  |  | 1.0 | 1.0 |
|  | Quercetin |  |  |  | 0.3 |  |  |  |  |  |  |
|  | Kaoliang |  |  |  |  |  |  |  |  | 2.0 |  |
|  | Oxybenzone-4 |  |  |  |  |  |  |  |  |  | 1.5 |
|  | Ethanol | 5 | 5 | 5 | 5 | 5 | 5 | 5 | 5 | 5 | 5 |
|  | Benzyl alcohol | 10 | 10 | 10 | 10 | 10 | 10 | 10 | 10 | 10 | 10 |
|  | Sodium hydroxide | q.s. | q.s. | q.s. | q.s. | q.s. | q.s. | q.s. | q.s. | q.s. | q.s. |
|  | Purified water | Balance | Balance | Balance | Balance | Balance | Balance | Balance | Balance | Balance | Balance |
|  | pH | 8 | 8 | 8 | 8 | 8 | 8 | 8 | 8 | 8 | 8 |
|  | Leaving time | 15 | 15 | 15 | 15 | 15 | 15 | 15 | 15 | 15 | 15 |
| Second agent | Ferrous sulfate | 1.0 | 1.0 | 1.0 | 1.0 | 1.0 | 1.0 | 1.0 | 1.0 | 1.0 | 1.0 |
|  | Glycol |  | 5.0 |  |  |  |  |  |  |  |  |
|  | Propylene glycol |  |  |  | 5.0 |  |  |  |  | 3.0 |  |
|  | Butylene glycol |  |  |  |  | 5.0 |  |  |  |  |  |
|  | Hexylene glycol |  |  |  |  |  | 5.0 |  |  | 3.0 |  |
|  | Glycerin |  |  |  |  |  |  | 5.0 |  |  |  |
|  | 3-Methyl-1,3-butanediol |  |  |  |  |  |  |  | 5.0 |  |  |
|  | Citric acid |  |  |  |  |  |  |  |  |  | 1.0 |
|  | Sodium hydroxide | q.s. | q.s. | q.s. | q.s. | q.s. | q.s. | q.s. | q.s. | q.s. | q.s. |
|  | Hydrochloric acid | q.s. | q.s. | q.s. | q.s. | q.s. | q.s. | q.s. | q.s. | q.s. | q.s. |
|  | Purified water | Balance | Balance | Balance | Balance | Balance | Balance | Balance | Balance | Balance | Balance |
|  | pH | 4 | 4 | 4 | 4 | 4 | 4 | 4 | 4 | 4 | 4 |
|  | Leaving time | 15 | 15 | 15 | 15 | 15 | 15 | 15 | 15 | 15 | 15 |
| Hair dyeing Results |  | ◎ | ◎ | ○ | ○ | ○ | ○ | ◎ | ◎ | ○ | X |
| Shampoo resistance |  | X | Δ | X | X | X | X | ○ | ○ | X | — |
| Stability of second agent |  | X | X | X | X | X | X | X | X | X | ○ |

*q.s.: quantum sufficiat (= appropriate amount)

The second agent of each of Examples 1-6 and 22 and Comparative Examples 1-8 was mixed with a first agent prepared by dissolving sodium salicylate in water/isopropanol. Thereafter, the prepared hair dye solutions were compared with one another in terms of coloring property (reactivity). The results are shown in Table 5.

TABLE 5

|  | Example 1 | Example 2 | Example 3 | Example 4 | Example 5 | Example 6 | Example 22 |
|---|---|---|---|---|---|---|---|
| Reaction rate | Low | Low | Low | Slightly Low | Slightly Low | Slightly Low | Low |

|  | Comparative Example 1 | Comparative Example 3 | Comparative Example 4 | Comparative Example 5 | Comparative Example 6 | Comparative Example 7 | Comparative Example 8 |
|---|---|---|---|---|---|---|---|
| Reaction rate | High | High | High | High | High | High | High |

It is assumed that samples with a high level of color loss have a high reaction rate and thereby color development (dyeing) occurs only around the surface of hair, whereas samples with a low level of color loss have a low reaction rate and thus the reaction (dyeing) is slowly carried out inside the hair (FIG. 1), so that the level of color loss is small. That is to say, the inside of the hair can also be dyed by suitably controlling the reaction rate, and as a result, a hair dye having only a small level of color loss can be provided.

The invention claimed is:

1. A hair dye, which comprises a combination of (1) a first agent containing a substance reacting with iron to develop color, and (2) a second agent containing (a) an iron salt and (b) at least one component selected from among xylitol, sorbitol, pentylene glycol, dipropylene glycol, triethylene glycol, erythritol and diglycerin.

2. The hair dye according to claim 1, wherein the at least one component selected from among xylitol, sorbitol, pentylene glycol, dipropylene glycol, triethylene glycol, erythritol and diglycerin is added in an equimolar amount or more based on the amount of iron salt, and at a weight percentage of 20% or less based on the total weight of the second agent.

3. The hair dye according to claim 1, wherein the component described in (2) (b) is at least one component selected from among xylitol, sorbitol, pentylene glycol and dipropylene glycol.

4. The hair dye according to claim 1, wherein the component described in (2) (b) is at least one component selected from xylitol and sorbitol.

5. The hair dye according to claim 1, wherein the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, luteolinidin, and oxybenzone.

6. The hair dye according to claim 2, wherein the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, luteolinidin, and oxybenzone.

7. The hair dye according to claim 3, wherein the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, luteolinidin, and oxybenzone.

8. The hair dye according to claim 4, wherein the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, luteolinidin, and oxybenzone.

9. The hair dye according to claim 1, wherein the iron salt is ferrous sulfate, ferrous chloride, ferrous acetate, ferric sulfate, ferric chloride, or ferric acetate.

10. The hair dye according to claim 2, wherein the iron salt is ferrous sulfate, ferrous chloride, ferrous acetate, ferric sulfate, ferric chloride, or ferric acetate.

11. The hair dye according to claim 3, wherein the iron salt is ferrous sulfate, ferrous chloride, ferrous acetate, ferric sulfate, ferric chloride, or ferric acetate.

12. The hair dye according to claim 4, wherein the iron salt is ferrous sulfate, ferrous chloride, ferrous acetate, term sulfate, ferric chloride, or ferric acetate.

13. The hair dye according to claim 5, wherein the iron salt is ferrous sulfate, ferrous chloride, ferrous acetate, ferric sulfate, ferric chloride, or ferric acetate.

14. The hair dye according to claim 1, wherein the substance reacting with iron to develop color is used at a weight percentage of 0.5% to 10% based on the total weight of the first agent, and the iron salt is used at a weight percentage of 0.5% to 10% based on the total weight of the second agent.

15. The hair dye according to claim 2, wherein the substance reacting with iron to develop color is used at a weight percentage of 0.5% to 10% based on the total weight of the first agent, and the iron salt is used at a weight percentage of 0.5% to 10% based on the total weight of the second agent.

16. The hair dye according to claim 3, wherein the substance reacting with iron to develop color is used at a weight percentage of 0.5% to 10% based on the total weight of the first agent, and the iron salt is used at a weight percentage of 0.5% to 10% based on the total weight of the second agent.

17. The hair dye according to claim 4, wherein the substance reacting with iron to develop color is used at a weight percentage of 0.5% to 10% based on the total weight of the first agent, and the iron salt is used at a weight percentage of 0.5% to 10% based on the total weight of the second agent.

18. The hair dye according to claim 5, wherein the substance reacting with iron to develop color is used at a weight percentage of 0.5% to 10% based on the total weight of the first agent, and the iron salt is used at a weight percentage of 0.5% to 10% based on the total weight of the second agent.

19. The hair dye according to claim 9, wherein the substance reacting with iron to develop color is used at a weight percentage of 0.5% to 10% based on the total weight of the first agent, and the iron salt is used at a weight percentage of 0.5% to 10% based on the total weight of the second agent.

20. A method for dyeing hair, which comprises adding the hair dye according to claim 1.

* * * * *